United States Patent
Lesko et al.

(10) Patent No.: US 11,058,472 B2
(45) Date of Patent: Jul. 13, 2021

(54) COMBINATION ULTRASONIC AND ELECTROSURGICAL INSTRUMENT HAVING CLAMP ARM ELECTRODE

(71) Applicant: ETHICON LLC, Guaynabo, PR (US)

(72) Inventors: Jason R. Lesko, Cincinnati, OH (US); Catherine A. Corbett, Cincinnati, OH (US); Craig T. Davis, Cincinnati, OH (US); Frederick L. Estera, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 388 days.

(21) Appl. No.: 15/967,753

(22) Filed: May 1, 2018

(65) Prior Publication Data

US 2018/0333181 A1 Nov. 22, 2018

Related U.S. Application Data

(60) Provisional application No. 62/509,351, filed on May 22, 2017.

(51) Int. Cl.
*A61B 18/14* (2006.01)
*A61B 18/00* (2006.01)
(Continued)

(52) U.S. Cl.
CPC ...... *A61B 18/00* (2013.01); *A61B 17/320092* (2013.01); *A61B 18/1206* (2013.01);
(Continued)

(58) Field of Classification Search
CPC .... A61B 17/320068; A61B 17/320092; A61B 2017/00017; A61B 2017/00137;
(Continued)

(56) References Cited

U.S. PATENT DOCUMENTS

| | | |
|---|---|---|
| 5,322,055 A | 6/1994 | Davison et al. |
| 5,400,267 A | 3/1995 | Denen et al. |

(Continued)

FOREIGN PATENT DOCUMENTS

| | | |
|---|---|---|
| DE | 10 2014 116065 A1 | 5/2016 |
| EP | 2 371 314 A2 | 10/2011 |

(Continued)

OTHER PUBLICATIONS

International Search Report and Written Opinion dated Aug. 22, 2018 for Application No. PCT/US2018/033599, 14 pgs.

(Continued)

*Primary Examiner* — Linda C Dvorak
*Assistant Examiner* — Khadijeh A Vahdat
(74) *Attorney, Agent, or Firm* — Frost Brown Todd LLC

(57) ABSTRACT

A surgical instrument includes an ultrasonic transducer, a distally extending shaft, and an end effector at a distal end of the shaft. The end effector includes an ultrasonic blade and a clamp arm. The ultrasonic blade includes an upper treatment side, a lower treatment side, a first lateral side, and a second lateral side. The clamp arm is movable relative to the ultrasonic blade for clamping tissue therebetween, and it provides an RF electrode operable to seal tissue with RF energy. The RF electrode includes first and second electrode side portions. The first electrode side portion is spaced laterally outward from the first lateral side of the ultrasonic blade by a first lateral gap distance. The second electrode side portion spaced from the first electrode side portion and is spaced laterally outward from the second lateral side of the ultrasonic blade by a second lateral gap distance.

20 Claims, 9 Drawing Sheets

(51) Int. Cl.
*A61B 18/12* (2006.01)
*A61B 17/32* (2006.01)
*A61B 17/00* (2006.01)
*A61B 17/29* (2006.01)
*A61B 90/00* (2016.01)

(52) U.S. Cl.
CPC ............ *A61B 18/1445* (2013.01); *A61B 2017/00017* (2013.01); *A61B 2017/00137* (2013.01); *A61B 2017/2929* (2013.01); *A61B 2017/2932* (2013.01); *A61B 2017/320072* (2013.01); *A61B 2017/320074* (2017.08); *A61B 2017/320075* (2017.08); *A61B 2017/320078* (2017.08); *A61B 2017/320088* (2013.01); *A61B 2017/320094* (2017.08); *A61B 2017/320095* (2017.08); *A61B 2018/0063* (2013.01); *A61B 2018/00077* (2013.01); *A61B 2018/00083* (2013.01); *A61B 2018/00607* (2013.01); *A61B 2018/00988* (2013.01); *A61B 2018/00994* (2013.01); *A61B 2018/126* (2013.01); *A61B 2018/1452* (2013.01); *A61B 2018/1457* (2013.01); *A61B 2090/0803* (2016.02)

(58) Field of Classification Search
CPC ........... A61B 2017/00738; A61B 2017/00929; A61B 2017/2929; A61B 2017/2932; A61B 2017/320072; A61B 2017/320074; A61B 2017/320075; A61B 2017/320078; A61B 2017/320088; A61B 2017/320094; A61B 2017/320095; A61B 18/00; A61B 18/12; A61B 18/1206; A61B 18/1266; A61B 18/14; A61B 18/1442; A61B 18/1445; A61B 18/1448; A61B 2018/00077; A61B 2018/00083; A61B 2018/00136; A61B 2018/00178; A61B 2018/00577; A61B 2018/00607; A61B 2018/0063; A61B 2018/00988; A61B 2018/00994; A61B 2018/126; A61B 2018/142; A61B 2018/1452; A61B 2018/1457
USPC .......................... 606/51–52, 169, 205–207
See application file for complete search history.

(56) References Cited

U.S. PATENT DOCUMENTS

| | | |
|---|---|---|
| 5,792,135 A | 8/1998 | Madhani et al. |
| 5,817,084 A | 10/1998 | Jensen |
| 5,873,873 A | 2/1999 | Smith et al. |
| 5,878,193 A | 3/1999 | Wang et al. |
| 5,944,737 A | 8/1999 | Tsonton et al. |
| 5,980,510 A | 11/1999 | Tsonton et al. |
| 6,231,565 B1 | 5/2001 | Tovey et al. |
| 6,283,981 B1 | 9/2001 | Beaupre |
| 6,309,400 B2 | 10/2001 | Beaupre |
| 6,325,811 B1 | 12/2001 | Messerly |
| 6,364,888 B1 | 4/2002 | Niemeyer et al. |
| 6,423,082 B1 | 7/2002 | Houser et al. |
| 6,500,176 B1 | 12/2002 | Truckai et al. |
| 6,773,444 B2 | 8/2004 | Messerly |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,524,320 B2 | 4/2009 | Tierney et al. |
| 7,691,098 B2 | 4/2010 | Wallace et al. |
| 7,806,891 B2 | 10/2010 | Nowlin et al. |
| 8,025,630 B2 | 9/2011 | Murakami et al. |
| 8,057,498 B2 | 11/2011 | Robertson |
| 8,147,488 B2 | 4/2012 | Masuda |
| 8,461,744 B2 | 6/2013 | Wiener et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,591,536 B2 | 11/2013 | Robertson |
| 8,602,288 B2 | 12/2013 | Shelton, IV et al. |
| 8,616,431 B2 | 12/2013 | Timm et al. |
| 8,623,027 B2 | 1/2014 | Price et al. |
| 8,663,220 B2 | 3/2014 | Wiener et al. |
| 8,783,541 B2 | 7/2014 | Shelton, IV et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 8,939,974 B2 | 1/2015 | Boudreaux et al. |
| 8,986,302 B2 | 3/2015 | Aldridge et al. |
| 9,017,326 B2 | 4/2015 | DiNardo et al. |
| 9,039,690 B2 | 5/2015 | Kersten et al. |
| 9,089,327 B2 | 7/2015 | Worrell et al. |
| 9,095,367 B2 | 8/2015 | Olson et al. |
| 9,101,385 B2 | 8/2015 | Shelton, IV et al. |
| 9,107,690 B2 | 8/2015 | Bales, Jr. et al. |
| 9,161,803 B2 | 10/2015 | Yates et al. |
| 9,237,921 B2 | 1/2016 | Messerly et al. |
| 9,301,759 B2 | 4/2016 | Spivey et al. |
| 9,402,682 B2 | 8/2016 | Worrell et al. |
| 9,545,253 B2 | 1/2017 | Worrell et al. |
| 9,572,622 B2 | 2/2017 | Shelton, IV et al. |
| 9,681,912 B2 | 6/2017 | Tsubuku et al. |
| 9,724,120 B2 | 8/2017 | Faller et al. |
| 9,901,754 B2 | 2/2018 | Yamada |
| 9,962,222 B2 | 5/2018 | Brustad et al. |
| 10,010,340 B2 | 7/2018 | Hibner et al. |
| 10,028,765 B2 | 7/2018 | Hibner et al. |
| 10,039,595 B2 | 8/2018 | Sakaguchi et al. |
| 10,201,364 B2 | 2/2019 | Leimbach et al. |
| 2007/0016236 A1 | 1/2007 | Beaupre |
| 2010/0036405 A1* | 2/2010 | Giordano ............ A61B 5/6847 606/169 |
| 2012/0078243 A1 | 3/2012 | Worrell et al. |
| 2014/0135804 A1 | 5/2014 | Weisenburgh, II et al. |
| 2014/0163541 A1 | 6/2014 | Shelton, IV et al. |
| 2014/0239037 A1 | 8/2014 | Boudreaux et al. |
| 2015/0088178 A1 | 3/2015 | Stulen et al. |
| 2015/0141981 A1 | 5/2015 | Price et al. |
| 2015/0164538 A1 | 6/2015 | Aldridge et al. |
| 2015/0358426 A1 | 12/2015 | Kimball et al. |
| 2015/0374360 A1 | 12/2015 | Scheib et al. |
| 2016/0022305 A1 | 1/2016 | Lamping et al. |
| 2016/0302820 A1 | 10/2016 | Hibner et al. |
| 2016/0324537 A1 | 11/2016 | Green et al. |
| 2016/0367281 A1 | 12/2016 | Gee et al. |
| 2017/0000515 A1 | 1/2017 | Akagane |
| 2017/0000516 A1 | 1/2017 | Stulen et al. |
| 2017/0000541 A1 | 1/2017 | Yates et al. |
| 2017/0086876 A1 | 3/2017 | Wiener et al. |
| 2017/0086908 A1 | 3/2017 | Wiener et al. |
| 2017/0086909 A1 | 3/2017 | Yates et al. |
| 2017/0086910 A1 | 3/2017 | Wiener et al. |
| 2017/0086911 A1 | 3/2017 | Wiener et al. |
| 2017/0105754 A1 | 4/2017 | Boudreaux et al. |
| 2017/0119425 A1* | 5/2017 | Hibner ........... A61B 17/320092 |
| 2018/0116688 A1 | 5/2018 | Akagane |
| 2018/0333182 A1 | 11/2018 | Clauda |

FOREIGN PATENT DOCUMENTS

| | | |
|---|---|---|
| EP | 2 478 861 A2 | 7/2012 |
| EP | 2 641 552 A2 | 9/2013 |
| EP | 3 031 417 A1 | 6/2016 |
| EP | 3 117 790 A1 | 1/2017 |
| EP | 3 287 085 A1 | 2/2018 |

(56) References Cited

FOREIGN PATENT DOCUMENTS

| WO | WO 2016/091400 | A1 | 6/2016 |
|----|----------------|----|--------|
| WO | WO 2017/027853 | A1 | 2/2017 |
| WO | WO 2017/058617 | A2 | 4/2017 |
| WO | WO 2017/091377 | A1 | 6/2017 |
| WO | WO 2017/100427 | A2 | 6/2017 |

OTHER PUBLICATIONS

International Search Report and Written Opinion dated Jan. 2, 2019 for Application No. PCT/US2018/033603, 23 pgs.
International Search Report and Written Opinion dated Nov. 6, 2018 for Application No. PCT/US2018/033605, 14 pgs.
International Search Report and Written Opinion dated Jan. 2, 2019 for Application No. PCT/US2018/033607, 22 pgs.
International Search Report and Written Opinion dated Nov. 6, 2018 for Application No. PCT/US2018/033608, 14 pgs.
International Search Report and Written Opinion dated Sep. 3, 2018 for Application No. PCT/US2018/033615, 13 pgs.
International Search Report and Written Opinion dated Aug. 22, 2018 for Application No. PCT/US2018/033618, 12 pgs.
International Search Report and Written Opinion dated Oct. 19, 2018 for Application No. PCT/US2018/033619, 20 pgs.
U.S. Appl. No. 62/509,351, entitled "Ultrasonic Instrument With Electrosurgical Features," filed May 22, 2017.
U.S. Appl. No. 15/967,740, entitled "Combination Ultrasonic and Electrosurgical Instrument Having Electrical Circuits with Shared Return Path," filed May 1, 2018.
U.S. Appl. No. 15/967,746, entitled "Combination Ultrasonic and Electrosurgical Instrument Having Slip Ring Electrical Contact Assembly," filed May 1, 2018.
U.S. Appl. No. 15/967,747, entitled "Combination Ultrasonic and Electrosurgical Instrument Having Electrically Insulating Features," filed May 1, 2018.
U.S. Appl. No. 15/967,751, entitled "Combination Ultrasonic and Electrosurgical Instrument Having Curved Ultrasonic Blade," filed May 1, 2018.
U.S. Appl. No. 15/967,759, entitled "Combination Ultrasonic and Electrosurgical Instrument Having Ultrasonic Waveguide with Distal Overmold Member," filed May 1, 2018.
U.S. Appl. No. 15/967,761, entitled "Combination Ultrasonic and Electrosurgical System Having Generator Filter Circuitry," filed May 1, 2018.
U.S. Appl. No. 15/967,763, entitled "Combination Ultrasonic and Electrosurgical Instrument with Adjustable Energy Modalities and Method for Sealing Tissue and Inhibiting Tissue Resection," filed May 1, 2018.
U.S. Appl. No. 15/967,764, entitled "Combination Ultrasonic and Electrosurgical System Having EEPROM and ASIC Components," filed May 1, 2018.
U.S. Appl. No. 15/967,770, entitled "Combination Ultrasonic and Electrosurgical Instrument with a Production Clamp Force Based Ultrasonic Seal Process and Related Methods," filed May 1, 2018.
U.S. Appl. No. 15/967,775, entitled "Combination Ultrasonic and Electrosurgical Instrument with Adjustable Energy Modalities and Method for Limiting Blade Temperature," filed May 1, 2018.
U.S. Appl. No. 15/967,777, entitled "Combination Ultrasonic and Electrosurgical Instrument and Method for Sealing Tissue with Various Termination Parameters," filed May 1, 2018.
U.S. Appl. No. 15/967,784, entitled "Combination Ultrasonic and Electrosurgical Instrument and Method for Sealing Tissue in Successive Phases," filed May 1, 2018.

* cited by examiner

COMBINATION ULTRASONIC AND ELECTROSURGICAL INSTRUMENT HAVING CLAMP ARM ELECTRODE

This application claims the benefit of U.S. Provisional App. No. 62/509,351, entitled "Ultrasonic Instrument With Electrosurgical Features," filed May 22, 2017, the disclosure of which is incorporated by reference herein.

BACKGROUND

Ultrasonic surgical instruments utilize ultrasonic energy for both precise cutting and controlled coagulation of tissue. The ultrasonic energy cuts and coagulates by vibrating a blade in contact with the tissue. Vibrating at frequencies of approximately 50 kilohertz (kHz), for example, the ultrasonic blade denatures protein in the tissue to form a sticky coagulum. Pressure exerted on the tissue with the blade surface collapses blood vessels and allows the coagulum to form a hemostatic seal. The precision of cutting and coagulation may be controlled by the surgeon's technique and adjusting the power level, blade edge, tissue traction, and blade pressure, for example.

Examples of ultrasonic surgical devices include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; U.S. Pat. No. 9,095,367, entitled "Flexible Harmonic Waveguides/Blades for Surgical Instruments," issued Aug. 4, 2015, the disclosure of which is incorporated by reference herein; and U.S. Pub. No. 2016/0022305, entitled "Ultrasonic Blade Overmold," published Jan. 28, 2016, issued as U.S. Pat. No. 9,750,521 on Sep. 5, 2017, the disclosure of which is incorporated by reference herein.

Electrosurgical instruments utilize electrical energy for sealing tissue, and generally include a distally mounted end effector that can be configured for bipolar or monopolar operation. During bipolar operation, electrical current is provided through the tissue by active and return electrodes of the end effector. During monopolar operation, current is provided through the tissue by an active electrode of the end effector and a return electrode (e.g., a grounding pad) separately located on a patient's body. Heat generated by the current flowing through the tissue may form hemostatic seals within the tissue and/or between tissues, and thus may be particularly useful for sealing blood vessels, for example. The end effector of an electrosurgical device may also include a cutting member that is movable relative to the tissue and the electrodes to transect the tissue.

Electrical energy applied by an electrosurgical device can be transmitted to the instrument by a generator coupled with the instrument. The electrical energy may be in the form of radio frequency ("RF") energy, which is a form of electrical energy generally in the frequency range of approximately 300 kilohertz (kHz) to 1 megahertz (MHz). In use, an electrosurgical device can transmit lower frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy works particularly well on connective tissue, which is primarily comprised of collagen and shrinks when contacted by heat.

An example of an RF electrosurgical device is the ENSEAL® Tissue Sealing Device by Ethicon Endo-Surgery, Inc., of Cincinnati, Ohio. Further examples of electrosurgical devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical devices and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 9,161,803, entitled "Motor Driven Electrosurgical Device with Mechanical and Electrical Feedback," issued Oct. 20, 2015, the disclosure of which is incorporated by reference herein; U.S. Pub. No. 2012/0078243, entitled "Control Features for Articulating Surgical Device," published Mar. 29, 2012, issued as U.S. Pat. No. 9,877,720 on Jan. 30, 2018, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; U.S. Pat. No. 9,545,253, entitled "Surgical Instrument with Contained Dual Helix Actuator Assembly," issued Jan. 17, 2017, the disclosure of which is incorporated by reference herein; and U.S. Pat. No. 9,572,622, entitled "Bipolar Electrosurgical Features for Targeted Hemostasis," issued Feb. 21, 2017, the disclosure of which is incorporated by reference herein.

Some instruments may provide ultrasonic and RF energy treatment capabilities through a single surgical device. Examples of such devices and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and U.S. Pub. No. 2017/0000541, entitled "Surgical Instrument with User Adaptable Techniques," published Jan. 5, 2017, the disclosure of which is incorporated by reference herein.

While various types of ultrasonic surgical instruments and electrosurgical instruments, including combination ultrasonic-electrosurgical instruments, have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
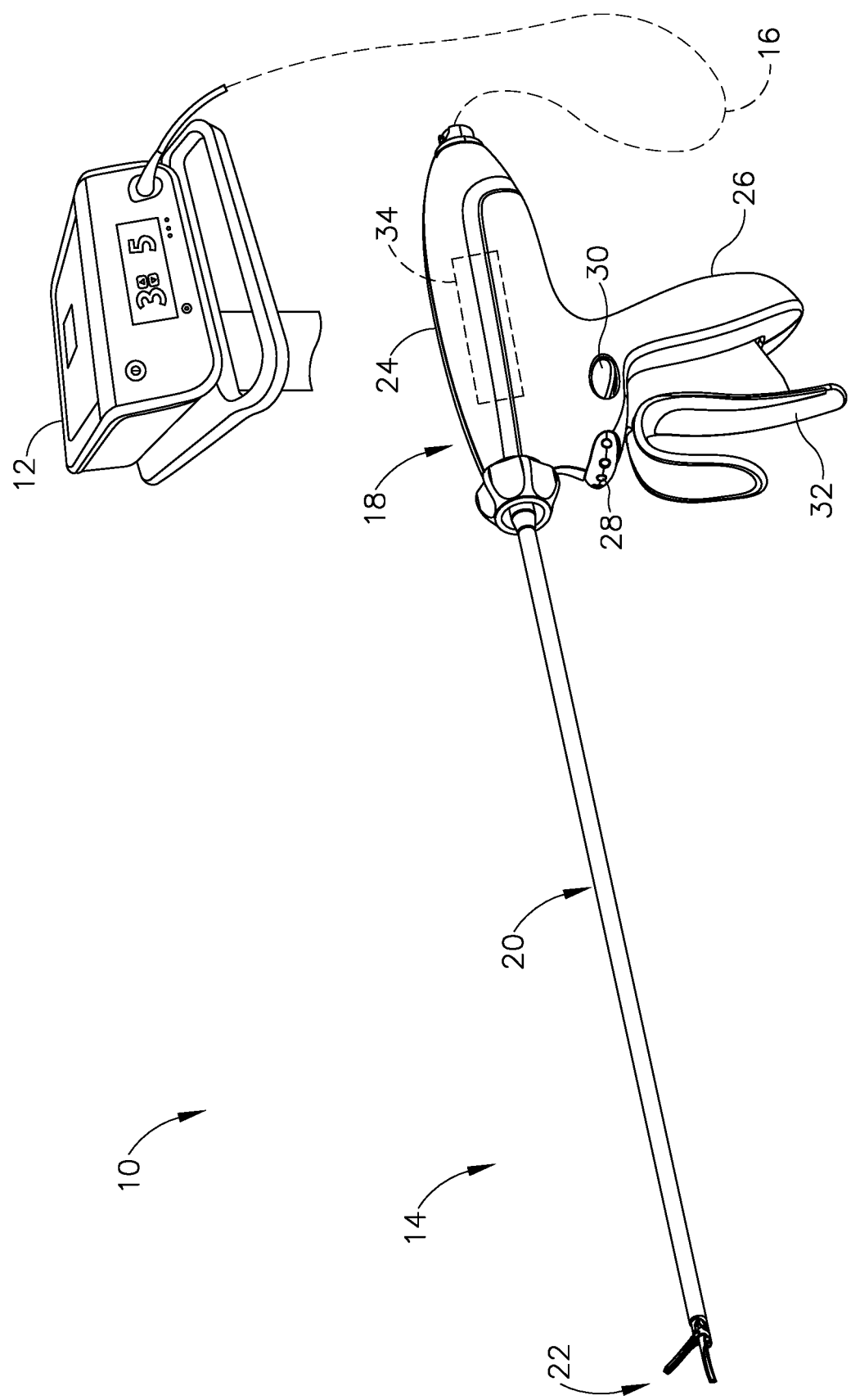
FIG. 1 depicts a perspective view of an exemplary surgical system having a generator and a surgical instrument operable to treat tissue with ultrasonic energy and bipolar RF energy.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

I. Exemplary Surgical System

FIG. 1 depicts an exemplary surgical system (10) including a generator (12) and a surgical instrument (14). Surgical instrument (14) is operatively coupled with the generator (12) via power cable (16). As described in greater detail below, generator (12) is operable to power surgical instrument (14) to deliver ultrasonic energy for cutting tissue, and electrosurgical bipolar RF energy (i.e., therapeutic levels of RF energy) for sealing tissue. In exemplary configurations, generator (12) is configured to power surgical instrument (14) to deliver ultrasonic energy and electrosurgical bipolar RF energy simultaneously.

A. Overview of Exemplary Surgical Instrument with Ultrasonic and Electrosurgical Features Surgical instrument (14) of the present example comprises a handle assembly (18), a shaft assembly (20) extending distally from the handle assembly (18), and an end effector (22) arranged at a distal end of the shaft assembly (20). Handle assembly (18) comprises a body (24) including a pistol grip (26) and energy control buttons (28, 30) configured to be manipulated by a surgeon. A trigger (32) is coupled to a lower portion of body (24) and is pivotable toward and away from pistol grip (26) to selectively actuate end effector (22), as described in greater detail below. In other suitable variations of surgical instrument (14), handle assembly (18) may comprise a scissor grip configuration, for example. As described in greater detail below, an ultrasonic transducer (34) is housed internally within and supported by body (24). In other configurations, ultrasonic transducer (34) may be provided externally of body (24).

Figure 2:
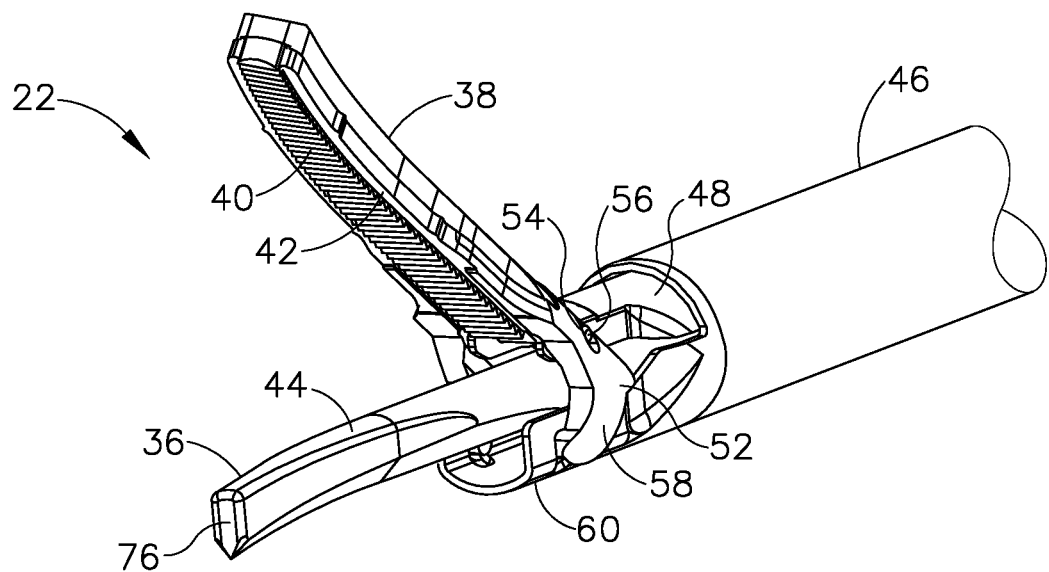
FIG. 2 depicts a top perspective view of an end effector of the surgical instrument of FIG. 1, having a clamp arm that provides a first electrode and an ultrasonic blade that provides a second electrode.
Figure 3:
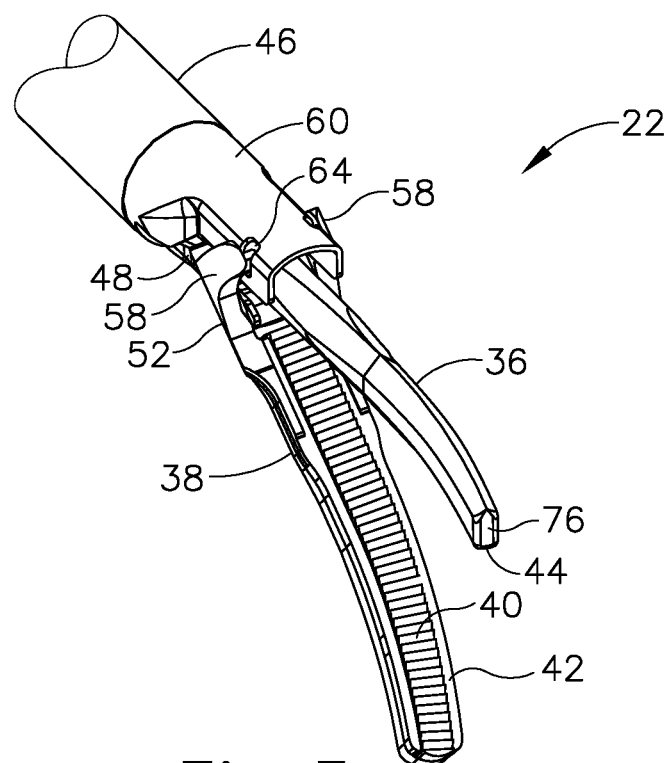
FIG. 3 depicts a bottom perspective view of the end effector of FIG. 2.

As shown in FIGS. 2 and 3, end effector (22) includes an ultrasonic blade (36) and a clamp arm (38) configured to selectively pivot toward and away from ultrasonic blade (36), for clamping tissue therebetween. Ultrasonic blade (36) is acoustically coupled with ultrasonic transducer (34), which is configured to drive (i.e., vibrate) ultrasonic blade (36) at ultrasonic frequencies for cutting and/or sealing tissue positioned in contact with ultrasonic blade (36). Clamp arm (38) is operatively coupled with trigger (32) such that clamp arm (38) is configured to pivot toward ultrasonic blade (36), to a closed position, in response to pivoting of trigger (32) toward pistol grip (26). Further, clamp arm (38) is configured to pivot away from ultrasonic blade (36), to an open position (see e.g., FIGS. 1-3), in response to pivoting of trigger (32) away from pistol grip (26). Various suitable ways in which clamp arm (38) may be coupled with trigger (32) will be apparent to those of ordinary skill in the art in view of the teachings provided herein. In some versions, one or more resilient members may be incorporated to bias clamp arm (38) and/or trigger (32) toward the open position.

A clamp pad (40) is secured to and extends distally along a clamping side of clamp arm (38), facing ultrasonic blade (36). Clamp pad (40) is configured to engage and clamp tissue against a corresponding tissue treatment portion of ultrasonic blade (36) when clamp arm (38) is actuated to its closed position. At least a clamping-side of clamp arm (38) provides a first electrode (42), referred to herein as clamp arm electrode (42). Additionally, at least a clamping-side of ultrasonic blade (36) provides a second electrode (44), referred to herein as a blade electrode (44). As described in greater detail below, electrodes (42, 44) are configured to apply electrosurgical bipolar RF energy, provided by generator (12), to tissue electrically coupled with electrodes (42, 44). Clamp arm electrode (42) may serve as an active electrode while blade electrode (44) serves as a return electrode, or vice-versa. Surgical instrument (14) may be configured to apply the electrosurgical bipolar RF energy through electrodes (42, 44) while vibrating ultrasonic blade (36) at an ultrasonic frequency, before vibrating ultrasonic blade (36) at an ultrasonic frequency, and/or after vibrating ultrasonic blade (36) at an ultrasonic frequency.

As shown in FIGS. 1-5, shaft assembly (20) extends along a longitudinal axis and includes an outer tube (46), an inner tube (48) received within outer tube (46), and an ultrasonic waveguide (50) supported within inner tube (48). As seen best in FIGS. 2-5, clamp arm (38) is coupled to distal ends of inner and outer tubes (46, 48). In particular, clamp arm (38) includes a pair of proximally extending clevis arms (52) that receive therebetween and pivotably couple to a distal end (54) of inner tube (48) with a pivot pin (56) received within through bores formed in clevis arms (52) and distal end (54) of inner tube (48). First and second clevis fingers (58) depend downwardly from clevis arms (52) and pivotably couple to a distal end (60) of outer tube (46). Specifically, each clevis finger (58) includes a protrusion (62) that is rotatably received within a corresponding opening (64) formed in a sidewall of distal end (60) of outer tube (46).

In the present example, inner tube (48) is longitudinally fixed relative to handle assembly (18), and outer tube (46) is configured to translate relative to inner tube (48) and handle assembly (18), along the longitudinal axis of shaft assembly (20). As outer tube (46) translates distally, clamp arm (38) pivots about pivot pin (56) toward its open position. As outer tube (46) translates proximally, clamp arm (38) pivots in an opposite direction toward its closed position. A proximal end of outer tube (46) is operatively coupled with trigger (32), for example via a linkage assembly, such that actuation of trigger (32) causes translation of outer tube (46) relative to inner tube (48), thereby opening or closing clamp arm (38). In other suitable configurations not shown herein, outer tube (46) may be longitudinally fixed and inner tube (48) may be configured to translate for moving clamp arm (38) between its open and closed positions.

Shaft assembly (20) and end effector (22) are configured to rotate together about the longitudinal axis, relative to handle assembly (18). A retaining pin (66), shown in FIG. 4, extends transversely through proximal portions of outer tube (46), inner tube (48), and waveguide (50) to thereby couple these components rotationally relative to one another. In the present example, a rotation knob (68) is provided at a proximal end portion of shaft assembly (20) to facilitate rotation of shaft assembly (20), and end effector (22), relative to handle assembly (18). Rotation knob (68) is secured rotationally to shaft assembly (20) with retaining pin (66), which extends through a proximal collar of rotation knob (68). It will be appreciated that in other suitable configurations, rotation knob (68) may be omitted or substituted with alternative rotational actuation structures.

Figure 5:
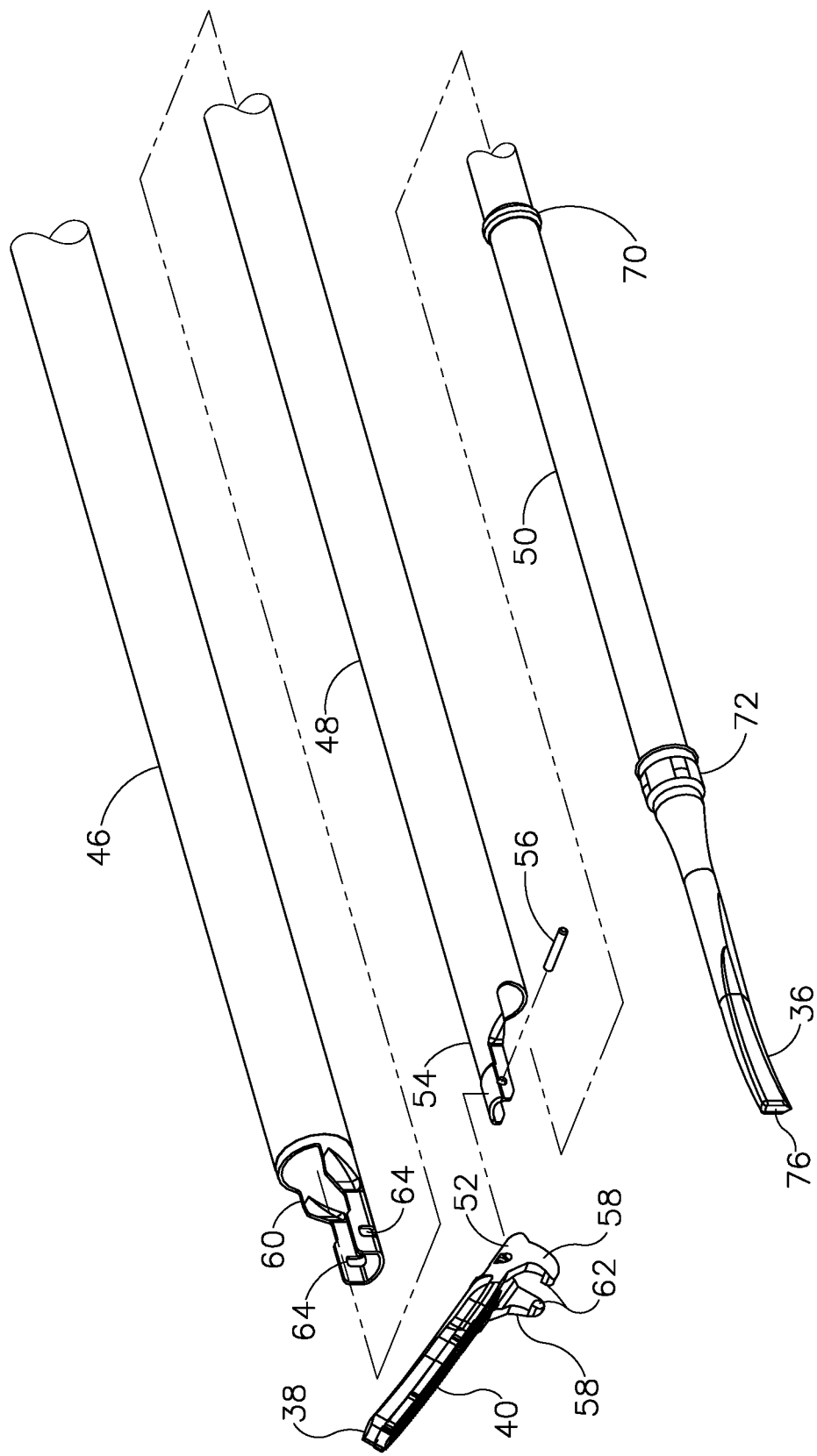
FIG. 5 depicts an enlarged exploded perspective view of a distal portion of the shaft assembly and the end effector of the surgical instrument of FIG. 1.

Ultrasonic waveguide (50) is acoustically coupled at its proximal end with ultrasonic transducer (34), for example by a threaded connection, and at its distal end with ultrasonic blade (36), as shown in FIG. 5. Ultrasonic blade (36) is shown formed integrally with waveguide (50) such that blade (36) extends distally, directly from the distal end of waveguide (50). In this manner, waveguide (50) acoustically couples ultrasonic transducer (34) with ultrasonic blade (36), and functions to communicate ultrasonic mechanical vibrations from transducer (34) to blade (36). Accordingly, ultrasonic transducer (34), waveguide (50), and ultrasonic blade (36) together define acoustic assembly (100). During use, ultrasonic blade (36) may be positioned in direct contact with tissue, with or without assistive clamping force provided by clamp arm (38), to impart ultrasonic vibrational energy to the tissue and thereby cut and/or seal the tissue. For example, blade (36) may cut through tissue clamped between clamp arm (38) and a first treatment side (204) of blade (36), or blade (36) may cut through tissue positioned in contact with an oppositely disposed second treatment side (206) of blade (36), for example during a "back-cutting" movement. In some variations, waveguide (50) may amplify the ultrasonic vibrations delivered to blade (36). Further, waveguide (50) may include various features operable to control the gain of the vibrations, and/or features suitable to tune waveguide (50) to a selected resonant frequency. Additional exemplary features of ultrasonic blade (36) and waveguide (50) are described in greater detail below.

Figure 4:
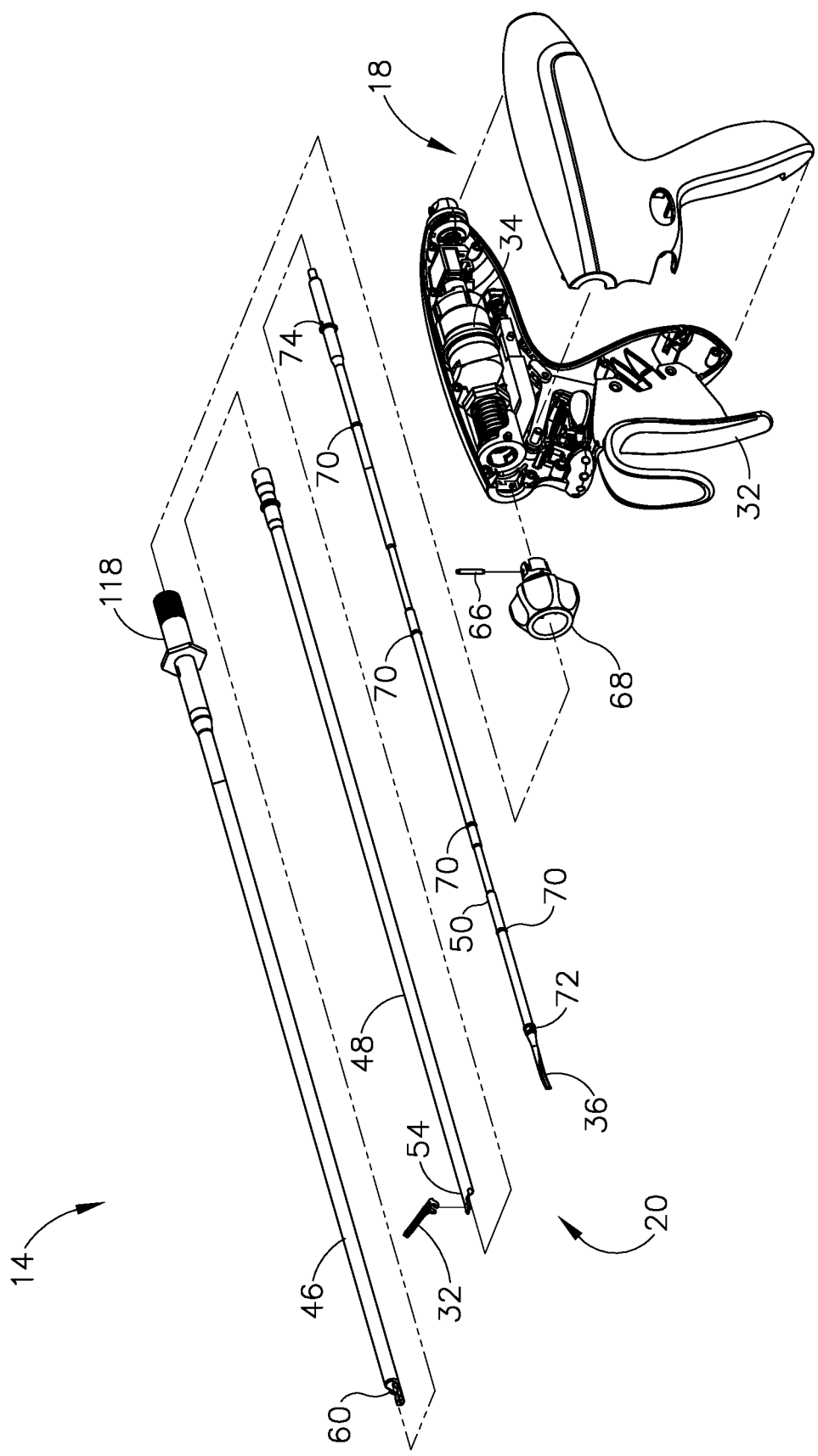
FIG. 4 depicts a partially exploded perspective view of the surgical instrument of FIG. 1.

Waveguide (50) is supported within inner tube (48) by a plurality of nodal support elements (70) positioned along a length of waveguide (50), as shown in FIGS. 4 and 5. Specifically, nodal support elements (70) are positioned longitudinally along waveguide (50) at locations corresponding to acoustic nodes defined by the resonant ultrasonic vibrations communicated through waveguide (50). Nodal support elements (70) may provide structural support to waveguide (50), and acoustic isolation between waveguide (50) and inner and outer tubes (46, 48) of shaft assembly (20). In exemplary variations, nodal support elements (70) may comprise o-rings. Waveguide (50) is supported at its distal-most acoustic node by a nodal support element in the form of an overmold member (72), shown in FIG. 5. Waveguide (50) is secured longitudinally and rotationally within shaft assembly (20) by retaining pin (66), which passes through a transverse through-bore (74) formed at a proximally arranged acoustic node of waveguide (50), such as the proximal-most acoustic node, for example.

In the present example, a distal tip (76) of ultrasonic blade (36) is located at a position corresponding to an anti-node associated with the resonant ultrasonic vibrations communicated through waveguide (50). Such a configuration enables the acoustic assembly (100) of instrument (14) to be tuned to a preferred resonant frequency $f_o$ when ultrasonic blade (36) is not loaded by tissue. When ultrasonic transducer (34) is energized by generator (12) to transmit mechanical vibrations through waveguide (50) to blade (36), distal tip (76) of blade (36) is caused to oscillate longitudinally in the range of approximately 20 to 120 microns peak-to-peak, for example, and in some instances in the range of approximately 20 to 50 microns, at a predetermined vibratory frequency $f_o$ of approximately 50 kHz, for example. When ultrasonic blade (36) is positioned in contact with tissue, the ultrasonic oscillation of blade (36) may simultaneously sever the tissue and denature the proteins in adjacent tissue cells, thereby providing a coagulative effect with minimal thermal spread.

Figure 6:
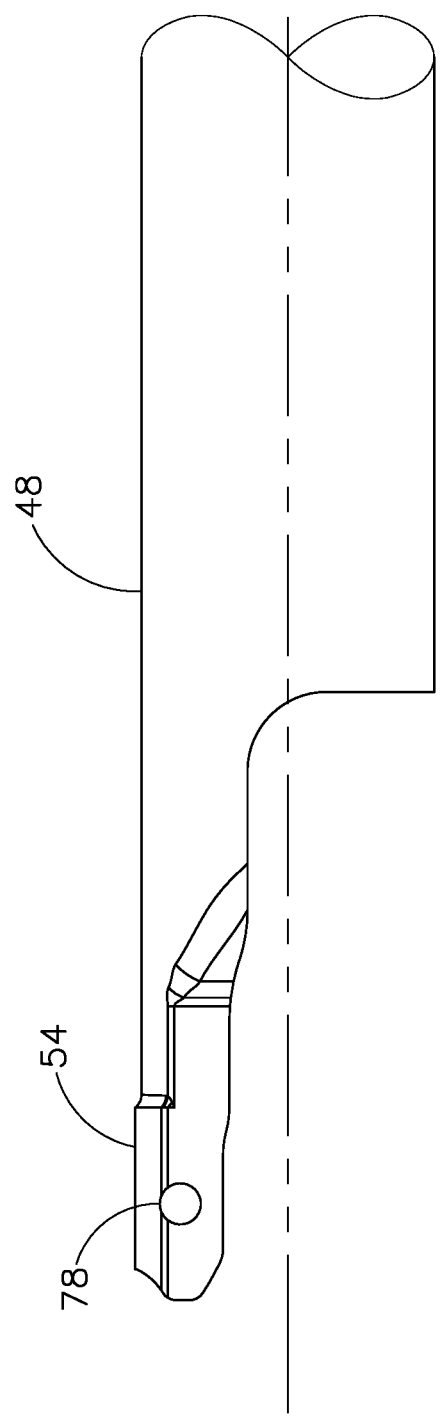
FIG. 6 depicts a side elevational view of a distal portion of an inner tube of the shaft assembly of the surgical instrument of FIG. 1.

As shown in FIG. 6, distal end (54) of inner tube (48) may be offset radially outwardly relative to a remaining proximal portion of inner tube (48). This configuration enables pivot pin bore (78), which receives clamp arm pivot pin (56), to be spaced further away from the longitudinal axis of shaft assembly (20) than if distal end (54) where formed flush with the remaining proximal portion of inner tube (48). Advantageously, this provides increased clearance between proximal portions of clamp arm electrode (42) and blade electrode (44), thereby mitigating risk of undesired "shorting" between electrodes (42, 44) and their corresponding active and return electrical paths, for example during back-cutting when ultrasonic blade (36) flexes toward clamp arm (38) and pivot pin (56) in response to normal force exerted on blade (36) by tissue. In other words, when ultrasonic blade (36) is used in a back-cutting operation, ultrasonic blade (36) may tend to deflect slightly away from the longitudinal axis of shaft assembly (20), toward pin (56). By having pivot pin bore (78) spaced further away from the longitudinal axis than pivot pin bore (78) otherwise would be in the absence of the radial offset provided by distal end (54) of the present example, distal end (54) provides additional lateral clearance between pivot pin (56) and ultrasonic blade (36), thereby reducing or eliminating the risk of contact between ultrasonic blade (36) and pivot pin (56) when ultrasonic blade (36) deflects laterally during back-cutting operations. In addition to preventing electrical short circuits that would otherwise result from contact between ultrasonic blade (36) and pivot pin (56) when end effector (22) is activated to apply RF electrosurgical energy, the additional clearance prevents mechanical damage that might otherwise result from contact between ultrasonic blade (36) and pivot pin (56) when ultrasonic blade (36) is vibrating ultrasonically.

B. Exemplary Ultrasonic Blades

Figure 7:
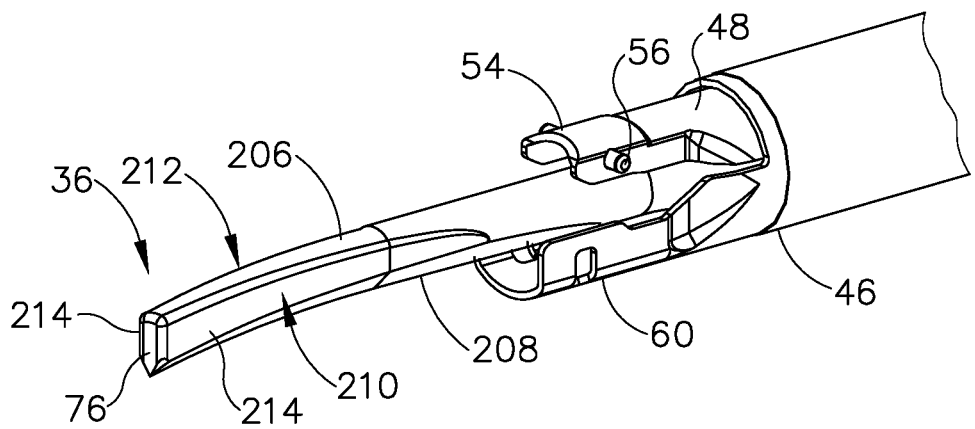
FIG. 7 depicts a perspective view of the ultrasonic blade and a distal portion of the shaft assembly of the surgical instrument of FIG. 1, with the clamp arm hidden from view.
Figure 8:
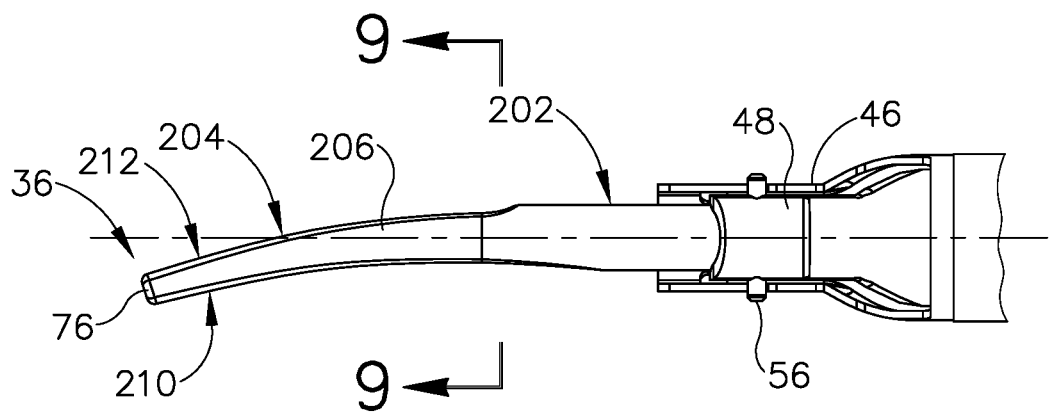
FIG. 8 depicts a top elevational view of the ultrasonic blade and distal portion of the shaft assembly of FIG. 7.
Figure 9:
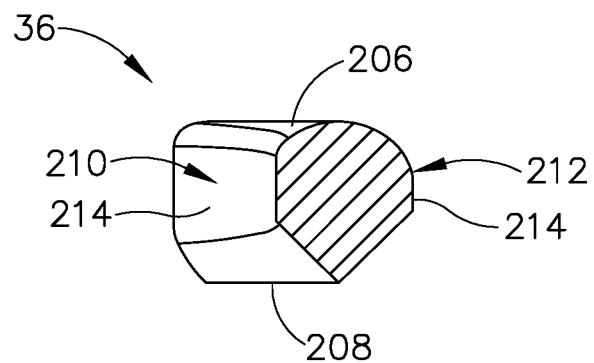
FIG. 9 depicts a sectional view of the ultrasonic blade of FIG. 7, taken along section line 9-9 of FIG. 8.

FIGS. 7-9 show additional details of ultrasonic blade (36) of surgical instrument (14). Ultrasonic blade (36) includes a tissue treatment portion that extends distally beyond inner tube and outer tube distal ends (54, 60), and terminates at distal tip (76) having filleted edges. Tissue treatment portion of blade (36) is configured to contact and treat tissue with ultrasonic energy received through ultrasonic waveguide (50). As shown in FIG. 8, the tissue treatment portion of blade (36) includes a proximal linear blade region (202) and a distal curved blade region (204) extending distally from linear blade region (202). Linear blade region (202) extends parallel to the longitudinal axis defined by shaft assembly (20), along which waveguide (50) extends. Curved blade region (204) extends along a curved path that deflects laterally away from the longitudinal axis in a distal direction. As shown best in FIG. 8, a lateral dimension of curved blade region (204) tapers distally toward distal tip (76). As shown in FIGS. 2 and 3, clamp arm (38) may be shaped similarly to treatment portion of ultrasonic blade (36) in that clamp arm (38) includes a proximal linear clamp portion and a distal curved clamp portion. In alternative configurations, ultrasonic blade (36) and clamp arm (38) may be entirely linear and extend parallel to the longitudinal axis.

Tissue treatment portion of ultrasonic blade (36) includes an upper primary treatment side (206) that faces clamp arm (38) (hidden from view) and is configured to compress tissue against clamp arm (38). Tissue treatment portion further includes a lower secondary treatment side having a cutting edge (208), arranged opposite of primary treatment side (206) and facing away from clamp arm (38). Cutting edge (208) is configured to cut tissue during back-cutting procedures. First and second lateral blade sides (210, 212) extend between primary treatment side (206) and cutting edge (208). As best shown in the sectional view of FIG. 9, primary treatment side (206) is convexly rounded. Additionally, each of first and second lateral sides (210, 212) includes a sweeping flat side surface (214) that extends distally through a distal portion of linear blade region (202) and an entirety of curved blade region (204), along the curved path thereof. As shown in FIG. 9, sweeping flat side surfaces (214) depend downwardly from the rounded treatment surface of primary treatment side (206), and define a cross-section of ultrasonic blade (36) having lateral side edges that are generally parallel to one another.

A blade height of ultrasonic blade (36) at a selected longitudinal location is defined by a maximum transverse distance measured between primary treatment side (206) and cutting edge (208) at the selected location. A blade width of ultrasonic blade (36) at a selected longitudinal location is defined by a maximum transverse distance measured between first and second lateral sides (210, 212) at the selected location. As shown in FIGS. 7 and 8, curved blade region (204) is shaped such that at various longitudinal locations therealong, including at blade tip (76), the blade height is greater than the corresponding blade width. In other configurations, the blade height may be less than or equal to the blade width.

C. Exemplary Configurations of Clamp Arm Electrode

Figure 10:
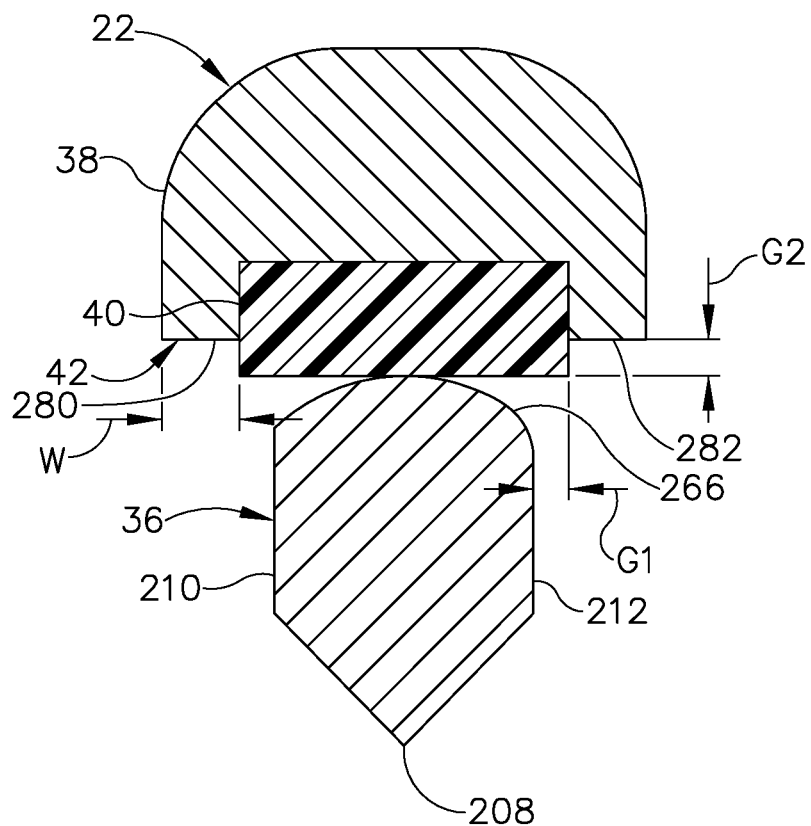
FIG. 10 depicts a schematic sectional end view of the end effector of the surgical instrument of FIG. 1, showing a clamp arm having a clamp pad and first and second electrode portions on either side of the clamp pad, indicating a lateral width of each electrode portion and a side gap distance between each electrode portion and a respective lateral side of the ultrasonic blade.

FIG. 10 shows a schematic sectional end view of a tissue treatment portion of end effector (22) of surgical instrument (14), including ultrasonic blade (36) and clamp arm (38) having clamp pad (40). Clamp pad (40) extends distally along a centerline region of the clamping side of clamp arm (38) and provides clamp arm electrode (42). Clamp arm electrode (42) includes a first electrode side portion (280) extending distally along a first lateral side of clamp pad (40), and a second electrode side portion (282) extending distally along an opposed second lateral side of clamp pad (40). As shown in FIG. 10, each clamp arm electrode side portion (280, 282) is formed with a lateral electrode width (W) measured from an outer lateral edge of the electrode side portion (280, 282) to an inner lateral edge of the electrode side portion (280, 282), shown abutting the corresponding lateral side of clamp pad (40). Clamp pad (40) is formed with a lateral pad width that is greater than a lateral width of ultrasonic blade (36), so as to define a lateral gap distance (G1) between an inner lateral edge of each clamp arm electrode side portion (280, 282) and the corresponding lateral side (210, 212) of blade (36). Clamp pad (40) protrudes beyond electrode side portions (280, 282) in a direction toward primary treatment side (266) of blade (36). This configuration defines a vertical gap distance (G2) between each electrode side portion (280, 282) and a clamping surface of clamp pad (40) and thus primary treatment side (266) of blade (36).

Optimal sizing of lateral electrode width (W) provides adequate electrode surface area for delivery of bipolar RF energy sufficient to seal tissue, while preventing unwanted electrical sparking or arcing caused by an electrode width (W) that is too small. Optimal sizing of gap distances (G1, G2) enables peak efficiency of end effector (22). For instance, optimal sizing of gap distances (G1, G2) prevents unwanted electrical shorting between ultrasonic blade (36) and clamp arm (38) caused by gap distances (G1, G2) that are too small, and further prevents unwanted electrical sparking or arcing and resulting inefficient transfer of RF energy caused by gap distances (G1, G2) that are too large. In exemplary configurations, lateral electrode width (W) of each clamp arm electrode side portion (280, 282) may be in the range of approximately 0.007 inches to approximately 0.018 inches, such as approximately 0.018 inches, for instance. Lateral gap distance (G1) corresponding to each electrode side portion (280, 282) may be in the range of approximately 0.002 inches to approximately 0.012 inches, such as approximately 0.007 inches or approximately 0.012 inches, for instance. Additionally, in various examples, vertical gap distances (G2) corresponding to electrode side portions (280, 282) are greater than 0 and may be uniform and equal to one another along an entire length of electrode side portions (280, 290).

Exemplary versions of clamp arm (38) and its dimensional configurations are described below, each of which is configured to function in a manner similar to clamp arm (38), and is suitable for use with surgical instrument (14). Furthermore, lateral electrode widths (W) and gap distances (G1, G2) of the additional clamp arm configurations described below may fall within the exemplary ranges described above. Persons skilled in the art will appreciate that various additional versions of clamp arm (38), incorporating any one or more of the exemplary clamp arm electrode features of the clamp arms described below, may be used in combination with surgical instrument (14).

Figure 11:
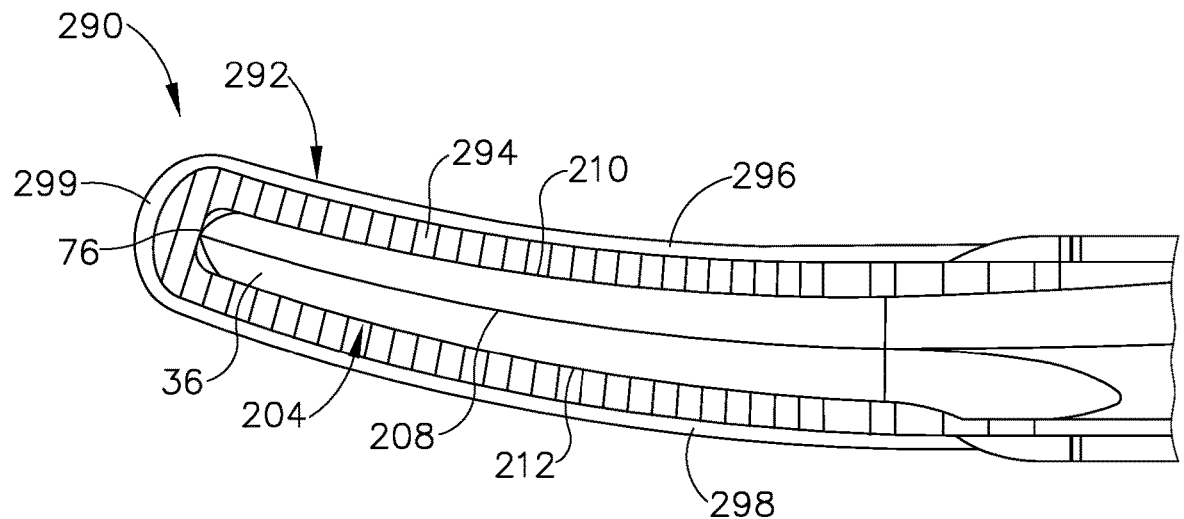
FIG. 11 depicts a bottom elevational view of an exemplary version of the end effector of FIG. 10, the version including a clamp arm having first and second electrode portions that each maintain a uniform lateral width and a uniform side gap distance along a tissue treatment portion of the ultrasonic blade.

FIG. 11 shows an end effector (290) including ultrasonic blade (36) and a clamp arm (292) according to a first exemplary version of clamp arm (38) of FIG. 10. Clamp arm (292) is similar to clamp arm (38) in that clamp arm (292) includes a centrally positioned clamp pad (294) and first and second clamp arm electrode side portions (296, 298) extending distally along respective lateral sides of clamp pad (294). Distal ends of clamp arm electrode side portions (296, 298) are joined together by a distal electrode bridge portion (299). As shown, the lateral electrode width (W) of each electrode side portion (296, 298) is uniform and equal to the other along an entire length of the treatment portion of ultrasonic blade (36). Similarly, the lateral gap distance (G1) corresponding to each electrode side portion (296, 298) is uniform and equal to the other along an entire length of the tissue treatment portion of ultrasonic blade (36). The lateral electrode widths W and the lateral gap distances G may fall within the ranges described above.

Figure 12:
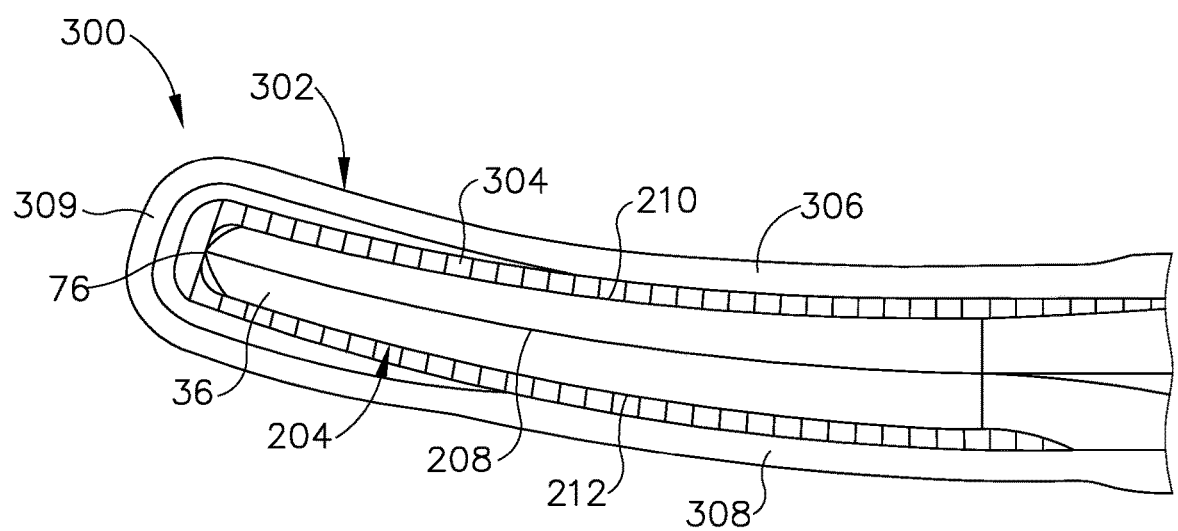
FIG. 12 depicts a bottom elevational view of another exemplary version of the end effector of FIG. 10, the version including a clamp arm having first and second electrode portions that each maintain a uniform lateral width and a non-uniform side gap distance that increases distally.

FIG. 12 shows an end effector (300) including ultrasonic blade (36) and a clamp arm (302) according to a second exemplary version of clamp arm (38) of FIG. 10. Clamp arm (302) is similar to clamp arm (292) of FIG. 11 in that clamp arm (302) includes a centrally positioned clamp pad (304) and first and second clamp arm electrode side portions (306, 308) extending distally along respective lateral sides of clamp pad (304) and joined at their distal ends by an electrode bridge portion (309). Clamp arm (302) is further similar to clamp arm (292) in that the lateral electrode width (W) of each electrode side portion (306, 308) is uniform and equal to the other along an entire length of the tissue treatment portion of ultrasonic blade (36).

Clamp arm (302) differs from clamp arm (292) in that lateral gap distance (G1) for each electrode side portion (306, 308) is non-uniform along the length of tissue treatment portion of blade (36). Specifically, lateral gap distances (G1) flare, or increase, distally along a distal portion of curved region (204) of blade (36). In the present example, lateral gap distance (G1) for electrode side portion (308) increases distally at a greater rate than lateral gap distance (G1) for electrode side portion (306). Accordingly, lateral gap distances (G1) for electrode side portions (306, 308) are not equal to one another throughout the distal portion of curved region (204) of blade (36). In particular, at various longitudinal locations along curved region (204) of blade (36), lateral gap distance (G1) for electrode side portion (308) is larger than lateral gap distance (G1) for electrode side portion (306). In other versions of clamp arm (302), lateral gap distances (G1) for electrode side portions (306, 308) may increase distally at the same rate such that gap distances (G1) remain equal to one another throughout curved blade region (204).

As shown in FIG. 12, the configuration of clamp arm (302) described above may be achieved by providing clamp pad (304) with a width that flares, or increases, laterally outward through the distal portion of curved blade region (204). Increased gap distances (G1) at the distal portion of end effector (300), where lateral deflection of ultrasonic blade (36) is greatest, allow for greater lateral misalignment between ultrasonic blade (36) and clamp arm (302) while maintaining electrical coupling therebetween, via clamped tissue. In order to maintain a uniform lateral electrode width (W) throughout the flared region of clamp pad (304), the lateral width of clamp arm (302) increases, or flares, distally simultaneously with the lateral width of clamp pad (304).

Figure 13:
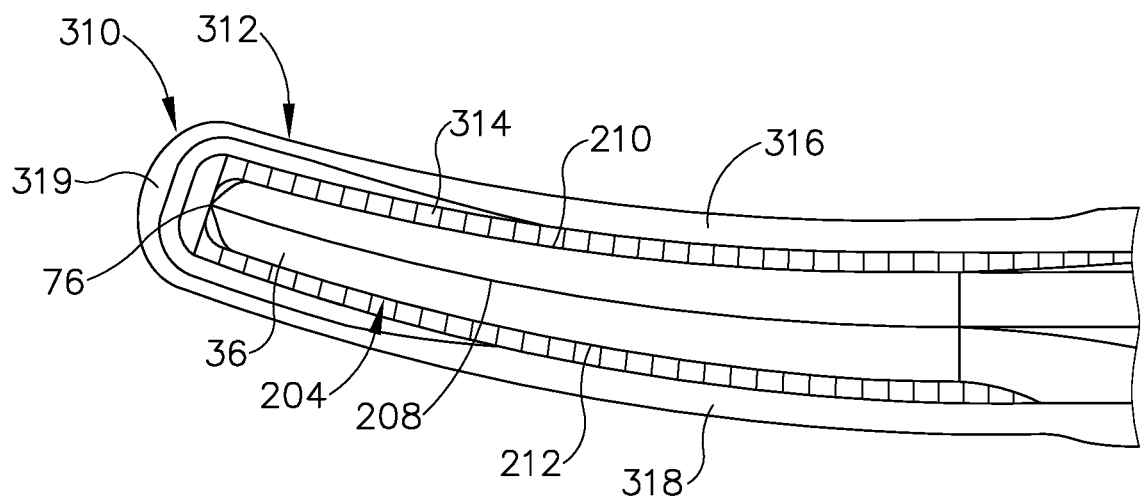
FIG. 13 depicts a bottom elevational view of another exemplary version of the end effector of FIG. 10, the version including a clamp arm having first and second electrode portions having non-uniform lateral widths that decrease distally, and non-uniform side gap distances that increase distally.

FIG. 13 shows an end effector (310) including ultrasonic blade (36) and a clamp arm (312) according to a third exemplary version of clamp arm (38) of FIG. 10. Clamp arm (312) is similar to clamp arm (302) of FIG. 12 in that clamp arm (312) includes a centrally positioned clamp pad (314) and first and second clamp arm electrode side portions (316, 318) extending distally along respective lateral sides of clamp pad (314) and joined at their distal ends by an electrode bridge portion (319). Clamp arm (312) is further similar to clamp arm (302) in that lateral gap distance (G1) for each electrode side portion (316, 318) increases distally along a distal portion of curved blade region (204), and gap distances (G1) are not equal to one another at all longitudinal locations throughout curved blade region (204).

Clamp arm (312) differs from clamp arm (302) in that the lateral electrode width (W) of each electrode side portion (316, 318) is non-uniform along the length of the tissue treatment portion of blade (36). Specifically, the lateral electrode widths (W) taper, or decrease, distally along the distal portion of curved blade region (204). In other words, as the lateral gap distances (G1) increase, the lateral electrode widths (W) decrease. The rates of increase and decrease may be similar to one another. Additionally, the lateral electrode widths (W) of electrode side portions (316, 318) may be substantially equal to each other at any given longitudinal location along clamp arm (312). The narrowed electrode side portions (316, 318) of clamp arm (302) deliver concentrated levels of bipolar RF energy at the clamp arm sections having increased gap distances (G1). This enables effective delivery of electrosurgical bipolar RF energy to tissue at the larger gap sections, which sections accommodate greater degrees of lateral deflection of ultrasonic blade (36) as described above, without requiring that a lateral width of clamp arm (312) flare outward like that of clamp arm (302) of FIG. 12. Accordingly, clamp arm (312) may generally provide the same performance benefits as clamp arm (302), while maintaining a slimmer profile.

Figure 14:
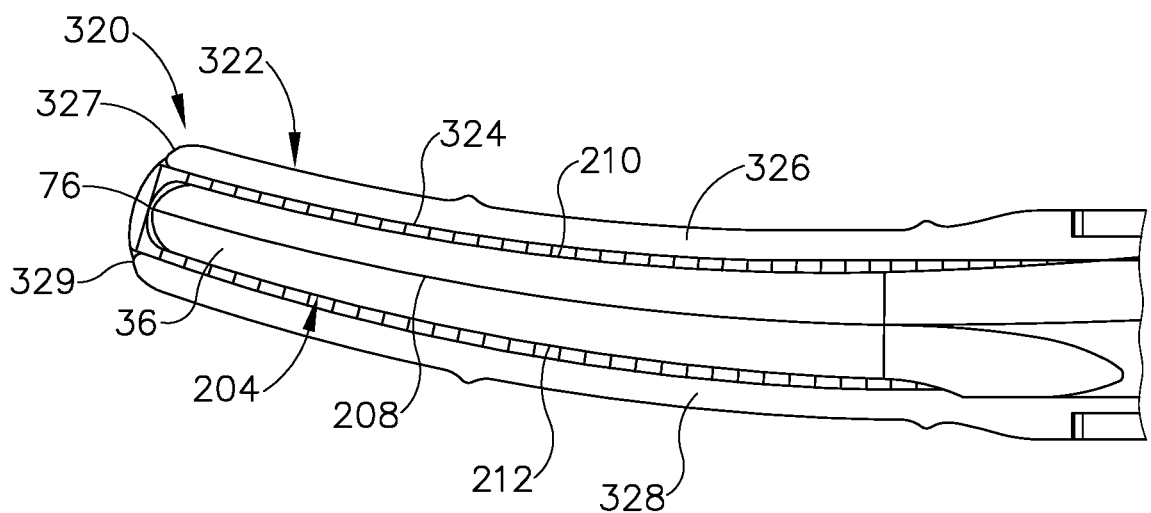
FIG. 14 depicts a bottom elevational view of another exemplary version of the end effector of FIG. 10, the version including a clamp arm having first and second electrode portions having distal ends that are separated from one another.

FIG. 14 shows an end effector (320) including ultrasonic blade (36) and a clamp arm (322) according to a fourth exemplary version of clamp arm (38) of FIG. 10. Clamp arm (322) is similar to clamp arms (292, 302, 312) described above in that clamp arm (322) includes a centrally positioned clamp pad (324) and first and second clamp arm electrode side portions (326, 328) extending distally along respective lateral sides of clamp pad (324). Additionally, lateral electrode width (W) of each electrode side portion (326, 328) is uniform and equal to the other along an entire length of the tissue treatment portion of ultrasonic blade (36).

Clamp arm (322) differs from clamp arms (292, 302, 312) in that clamp arm (322) omits a distal electrode bridge portion joining distal ends (327, 329) of electrode side portions (326, 328). Rather, in the present example, electrode distal ends (327, 329) are laterally separated from one another by clamp pad (324), which extends to a distal tip of clamp arm (322). Additionally, electrode distal ends (327, 329) align with distal blade tip (76), though it will be appreciated that distal ends (327, 329) may terminate proximally or distally of blade tip (76) in other examples. Though not shown, variations of any of clamp arms (292, 302, 312) described above may be provided in which distal electrode bridge portions (299, 309, 319) are omitted to provide electrode distal ends similar to distal ends (327, 329) of clamp arm (322).

Each clamp arm (292, 302, 312, 322) as described above has first and second electrode side portions that are equal in width (W) to one another along an entire length of the electrode side portions. However, alternative versions of clamp arms (292, 302, 312, 322) may have electrode side portions that are unequal in width (W) along one or more longitudinally extending portions thereof, for example along portions corresponding to curved blade region (204). Such variation in electrode widths (W) may be provided to accommodate differences in performance exhibited by blade (36) and/or clamp arm (292, 302, 312, 322) between their concave curved lateral sides, corresponding to first lateral blade side (210), and their respective convex curved lateral sides, corresponding to second lateral blade side (212). For example, during use, the concave curved lateral sides of blade (36) and clamp arm (292, 302, 312, 322) may provide a first degree of cutting and sealing treatment to tissue, while the convex curved lateral sides of blade (36) and clamp arm (292, 302, 312, 322) may provide a second degree of cutting and sealing treatment to tissue.

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) an ultrasonic transducer; (b) a shaft extending distally relative to the ultrasonic transducer; and (c) an end effector arranged at a distal end of the shaft, wherein the end effector comprises: (i) an ultrasonic blade configured to be driven by the ultrasonic transducer with ultrasonic energy, wherein the ultrasonic blade comprises: (A) an upper treatment side, (B) a lower treatment side arranged opposite of the upper treatment side, (C) a first lateral side, and (D) a second lateral side arranged opposite of the first lateral side, and (ii) a clamp arm movable relative to the ultrasonic blade for clamping tissue therebetween, wherein the clamp arm provides an RF electrode operable to seal tissue with RF energy, wherein the RF electrode comprises: (A) a first electrode side portion, wherein the first electrode side portion is spaced laterally outward from the first lateral side of the ultrasonic blade by a first lateral gap distance, and (B) a second electrode side portion spaced from the first electrode side portion, wherein the second electrode side portion is spaced laterally outward from the second lateral side of the ultrasonic blade by a second lateral gap distance.

Example 2

The surgical instrument of Example 1, wherein the end effector further comprises a clamp pad coupled to the clamp arm, wherein the first electrode side portion extends along a first lateral side of the clamp pad, wherein the second electrode side portion extends along a second lateral side of the clamp pad.

Example 3

The surgical instrument of any of the previous Examples, wherein the first lateral gap distance is equal to the second lateral gap distance along a curved distal portion of the ultrasonic blade.

Example 4

The surgical instrument of any of the previous Examples, wherein at least one of the first lateral gap distance or the second lateral gap distance is uniform along a curved distal portion of the ultrasonic blade.

Example 5

The surgical instrument of any of the previous Examples, wherein at least one of the first lateral gap distance or the second lateral gap distance is non-uniform along a curved distal portion of the ultrasonic blade.

Example 6

The surgical instrument of any of the previous Examples, wherein each of the first lateral gap distance and the second lateral gap distance is in the range of 0.002 inches to 0.012 inches along a curved distal portion of the ultrasonic blade.

Example 7

The surgical instrument of any of the previous Examples, wherein a lateral width of at least one of the first electrode side portion or the second electrode side portion is uniform along a length of at least a distal portion of the clamp arm.

Example 8

The surgical instrument of any of the previous Examples, wherein a lateral width of at least one of the first electrode side portion or the second electrode side portion is non-uniform along a length of at least a distal portion of the clamp arm.

Example 9

The surgical instrument of Example 8, wherein the lateral width of at least one of the first electrode side portion or the second electrode side portion increases distally.

Example 10

The surgical instrument of any of Examples 8 through 9, wherein the lateral width of at least one of the first electrode side portion or the second electrode side portion decreases distally

Example 11

The surgical instrument of any of the previous Examples, wherein a lateral width of each of the first electrode side portion and the second electrode side portion is in the range of 0.007 inches to 0.018 inches along a length of at least a distal portion of the clamp arm.

Example 12

The surgical instrument of any of the previous Examples, wherein the RF electrode extends distally beyond a distal tip of the ultrasonic blade and defines an electrode bridge portion that electrically couples a distal end of the first electrode side portion with a distal end of the second electrode side portion.

Example 13

The surgical instrument of any of the previous Examples, wherein the ultrasonic blade includes a linear proximal portion and a curved distal portion, wherein the first and second electrode side portions extend alongside the curved distal portion.

Example 14

The surgical instrument of any of the previous Examples, wherein the RF electrode comprises a first RF electrode, wherein the ultrasonic blade provides a second RF electrode, wherein the first and second RF electrodes are operable to seal tissue with bipolar RF energy.

Example 15

The surgical instrument of any of the previous Examples, wherein the upper treatment side of the ultrasonic blade includes a convexly curved surface that provides the second RF electrode.

Example 16

A surgical instrument comprising: (a) an ultrasonic transducer; (b) a shaft extending distally relative to the ultrasonic transducer; and (c) an end effector arranged at a distal end of the shaft, wherein the end effector comprises: (i) an ultrasonic blade configured to be driven by the ultrasonic transducer with ultrasonic energy, wherein the ultrasonic blade comprises: (A) an upper treatment side, (B) a lower treatment side arranged opposite of the upper treatment side, (C) a first lateral side, and (D) a second lateral side arranged opposite of the first lateral side, and (ii) a clamp arm movable relative to the ultrasonic blade for clamping tissue therebetween, wherein the clamp arm provides an RF electrode operable to seal tissue with RF energy, wherein the RF electrode comprises: (A) a first electrode side portion, wherein the first electrode side portion has a first width and is spaced laterally outward from the first lateral side of the ultrasonic blade by a first lateral gap distance, and (B) a second electrode side portion spaced from the first electrode side portion, wherein the second electrode side portion has a second width and is spaced laterally outward from the second lateral side of the ultrasonic blade by a second lateral gap distance, wherein at least one of the first width or the second width is non-uniform along a length of at least a distal portion of the clamp arm, wherein at least one of the first lateral gap distance or the second lateral gap distance is non-uniform along the length of at least the distal portion of the clamp arm.

Example 17

The surgical instrument of Example 16, wherein each of the first width and the second width decreases distally.

Example 18

The surgical instrument of any of Examples 16 through 17, wherein each of the first lateral gap distance and the second lateral gap distance increases distally.

Example 19

A surgical instrument comprising: (a) an ultrasonic transducer; (b) a shaft extending distally relative to the ultrasonic transducer; and (c) an end effector arranged at a distal end of the shaft, wherein the end effector comprises: (i) an ultrasonic blade configured to be driven by the ultrasonic transducer with ultrasonic energy, wherein the ultrasonic blade comprises: (A) a linear proximal blade portion, (B) a curved distal blade portion, (C) a first lateral side, and (D) a second lateral side arranged opposite of the first lateral side, and (ii) a clamp arm movable relative to the ultrasonic blade for clamping tissue therebetween, wherein the clamp arm provides an RF electrode operable to seal tissue with RF energy, wherein the RF electrode comprises: (A) a first electrode side portion, wherein the first electrode side portion is spaced laterally outward from the first lateral side of the ultrasonic blade by a first lateral gap distance, and (B) a second electrode side portion spaced from the first electrode side portion, wherein the second electrode side portion is spaced laterally outward from the second lateral side of the ultrasonic blade by a second lateral gap distance, wherein at least one of the first lateral gap distance or the second lateral gap distance is in the range of 0.002 inches to 0.012 inches along the curved distal blade portion.

Example 20

The surgical instrument of Example 19, wherein a lateral width of at least one of the first electrode side portion or the second electrode side portion is in the range of 0.007 inches to 0.018 inches along the curved distal blade portion.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. patent application Ser. No. 15/967,740, entitled "Combination Ultrasonic and Electrosurgical Instrument Having Electrical Circuits With Shared Return Path," filed on May 1, 2018, published as U.S. Pub. No. 2018/0333177 on Nov. 22, 2018; U.S. patent application Ser. No. 15/967,746, entitled "Combination Ultrasonic and Electrosurgical Instrument Having Slip Ring Electrical Contact Assembly," filed on May 1, 2018, published as U.S. Pub. No. 2018/0333178 on Nov. 22, 2018, issued as U.S. Pat. No. 10,945,778 on Mar. 16, 2021; U.S. patent application Ser. No. 15/967,747, entitled "Combination Ultrasonic and Electrosurgical Instrument Having Electrically Insulating Features," filed on May 1, 2018, published as U.S. Pub. No. 2018/0333179 on Nov. 22, 2018, issued as U.S. Pat. No. 10,945,779 on Mar. 16, 2021; U.S. patent application Ser. No. 15/967,751, entitled "Combination Ultrasonic and Electrosurgical Instrument Having Curved Ultrasonic Blade," filed on May 1, 2018, published as U.S. Pub. No. 2018/0333180 on Nov. 22, 2018; U.S. patent application Ser. No. 15/967,759, entitled "Combination Ultrasonic and Electrosurgical Instrument Having Ultrasonic Waveguide With Distal Overmold Member," filed on May 1, 2018, published as U.S. Pub. No. 2018/0333183 on Nov. 22, 2018; U.S. patent application Ser. No. 15/967,761, entitled "Combination Ultrasonic and Electrosurgical System Having Generator Filter Circuitry," filed on May 1, 2018, published as U.S. Pub. No. 2018/0333184 on Nov. 22, 2018; and/or U.S. patent application Ser. No. 15/967,764, entitled "Combination Ultrasonic and Electrosurgical System Having EEPROM and ASIC Components," filed on May 1, 2018, published as U.S. Pub. No. 2018/0333186 on Nov. 22, 2018. The disclosure of each of these applications is incorporated by reference herein.

Further, any one or more of the teachings, expressions, embodiments, examples, etc. described herein may be combined with any one or more of the teachings, expressions, embodiments, examples, etc. described in U.S. patent application Ser. No. 15/967,758, entitled "Combination Ultrasonic and Electrosurgical Instrument with Clamp Arm Position Input and Method for Identifying Tissue State," filed on May 1, 2018, published as U.S. Pub. No. 2018/0333182 on Nov. 22, 2018; U.S. patent application Ser. No. 15/967,763, entitled "Combination Ultrasonic and Electrosurgical Instrument with Adjustable Energy Modalities and Method for Sealing Tissue and Inhibiting Tissue Resection," filed on May 1, 2018, published as U.S. Pub. No. 2018/0333185 on Nov. 22, 2018; U.S. patent application Ser. No. 15/967,770, entitled "Combination Ultrasonic and Electrosurgical Instrument with Adjustable Clamp Force and Related Methods,"

filed on even date herewith May 1, 2018, published as U.S. Pub. No. 2018/0333187 on Nov. 22, 2018; U.S. patent application Ser. No. 15/967,775, entitled "Combination Ultrasonic and Electrosurgical Instrument with Adjustable Energy Modalities and Method for Limiting Blade Temperature," filed on May 1, 2018, published as U.S. Pub. No. 2018/0333188 on Nov. 22, 2018; U.S. patent application Ser. No. 15/967,777, entitled "Combination Ultrasonic and Electrosurgical Instrument and Method for Sealing Tissue with Various Termination Parameters," filed on May 1, 2018, published as U.S. Pub. No. 2018/0333189 on Nov. 22, 2018; and/or U.S. patent application Ser. No. 15/967,784, entitled "Combination Ultrasonic and Electrosurgical Instrument and Method for Sealing Tissue in Successive Phases," filed on May 1, 2018, published as U.S. Pub. No. 2018/0333190 on Nov. 22, 2018. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) an ultrasonic transducer;
   (b) a shaft extending distally relative to the ultrasonic transducer; and
   (c) an end effector arranged at a distal end of the shaft, wherein the end effector comprises:
      (i) an ultrasonic blade configured to be driven by the ultrasonic transducer with ultrasonic energy, wherein the ultrasonic blade comprises:
         (A) an upper treatment side,
         (B) a lower treatment side arranged opposite of the upper treatment side,
         (C) a first lateral side, and
         (D) a second lateral side arranged opposite of the first lateral side, and
      (ii) a clamp arm movable relative to the ultrasonic blade in a transverse direction from an open position to a closed position, wherein the clamp arm includes a clamp pad having a clamp pad surface defining a pad plane and facing toward the ultrasonic blade for clamping tissue therebetween, wherein the clamp arm provides an RF electrode operable to seal tissue with RF energy, wherein the RF electrode comprises:
         (A) a first electrode side portion, wherein the first electrode side portion is spaced in a lateral direction transverse to the transverse direction and laterally outward from the first lateral side of the ultrasonic blade by a first lateral gap distance, wherein the first electrode side portion is spaced in the transverse direction away from the pad plane and the ultrasonic blade a first transverse gap distance, and
         (B) a second electrode side portion spaced from the first electrode side portion, wherein the second electrode side portion is spaced in the lateral direction and laterally outward from the second lateral side of the ultrasonic blade by a second lateral gap distance, wherein the second electrode side portion is spaced in the transverse direction away from the pad plane and the ultrasonic blade a second transverse gap distance,
      wherein the clamp pad protrudes in the transverse direction beyond the first and second electrode side portions toward the upper treatment side of the ultrasonic blade such that the first and second electrode side portions are respectively the first and second transverse gap distances from the upper treatment side of the ultrasonic blade with the clamp arm in the closed position against the ultrasonic blade.

2. The surgical instrument of claim 1, wherein the end effector further comprises a clamp pad coupled to the clamp arm, wherein the first electrode side portion extends along a first lateral side of the clamp pad, wherein the second electrode side portion extends along a second lateral side of the clamp pad.

3. The surgical instrument of claim 1, wherein the first lateral gap distance is equal to the second lateral gap distance along a curved distal portion of the ultrasonic blade.

4. The surgical instrument of claim 1, wherein at least one of the first lateral gap distance or the second lateral gap distance is uniform along a curved distal portion of the ultrasonic blade.

5. The surgical instrument of claim 1, wherein at least one of the first lateral gap distance or the second lateral gap distance is non-uniform along a curved distal portion of the ultrasonic blade.

6. The surgical instrument of claim 1, wherein each of the first lateral gap distance and the second lateral gap distance is in the range of 0.002 inches to 0.012 inches along a curved distal portion of the ultrasonic blade.

7. The surgical instrument of claim 1, wherein a lateral width of at least one of the first electrode side portion or the second electrode side portion is uniform along a length of at least a distal portion of the clamp arm.

8. The surgical instrument of claim 1, wherein a lateral width of at least one of the first electrode side portion or the second electrode side portion is non-uniform along a length of at least a distal portion of the clamp arm.

9. The surgical instrument of claim 8, wherein the lateral width of at least one of the first electrode side portion or the second electrode side portion increases distally.

10. The surgical instrument of claim 8, wherein the lateral width of at least one of the first electrode side portion or the second electrode side portion decreases distally.

11. The surgical instrument of claim 1, wherein a lateral width of each of the first electrode side portion and the second electrode side portion is in the range of 0.007 inches to 0.018 inches along a length of at least a distal portion of the clamp arm.

12. The surgical instrument of claim 1, wherein the RF electrode extends distally beyond a distal tip of the ultrasonic blade and defines an electrode bridge portion that electrically couples a distal end of the first electrode side portion with a distal end of the second electrode side portion.

13. The surgical instrument of claim 1, wherein the ultrasonic blade includes a linear proximal portion and a curved distal portion, wherein the first and second electrode side portions extend alongside the curved distal portion.

14. The surgical instrument of claim 1, wherein the RF electrode comprises a first RF electrode, wherein the ultrasonic blade provides a second RF electrode, wherein the first and second RF electrodes are operable to seal tissue with bipolar RF energy.

15. The surgical instrument of claim 14, wherein the upper treatment side of the ultrasonic blade includes a convexly curved surface that provides the second RF electrode.

16. A surgical instrument comprising:
   (a) an ultrasonic transducer;
   (b) a shaft extending distally relative to the ultrasonic transducer; and
   (c) an end effector arranged at a distal end of the shaft and distally extending therefrom from a proximal end effector portion toward a distal end effector portion, wherein the end effector comprises:
(i) an ultrasonic blade configured to be driven by the ultrasonic transducer with ultrasonic energy, wherein the ultrasonic blade comprises:
   (A) an upper treatment side,
   (B) a lower treatment side arranged opposite of the upper treatment side,
   (C) a first lateral side, and
   (D) a second lateral side arranged opposite of the first lateral side, and
(ii) a clamp arm movable relative to the ultrasonic blade for clamping tissue therebetween, wherein the clamp arm provides an RF electrode operable to seal tissue with RF energy, wherein the RF electrode comprises:
   (A) a first electrode side portion, wherein the first electrode side portion has a first width and is spaced laterally outward from the first lateral side of the ultrasonic blade by a first lateral gap distance, and
   (B) a second electrode side portion spaced from the first electrode side portion, wherein the second electrode side portion has a second width and is spaced laterally outward from the second lateral side of the ultrasonic blade by a second lateral gap distance,
   wherein at least one of the first width or the second width is non-uniform along a distal length of at least a distal portion of the clamp arm,
   wherein at least one of the first lateral gap distance or the second lateral gap distance is non-uniform along the distal length of at least the distal portion of the clamp arm, and
   wherein each of the first and second lateral gap distances increases distally.

17. The surgical instrument of claim 16, wherein each of the first width and the second width decreases distally.

18. The surgical instrument of claim 16, wherein at least one of the first width or the second width is uniform along a proximal length of at least a proximal portion of the clamp arm, wherein at least one of the first lateral gap distance or the second lateral gap distance is uniform along the proximal length of at least the proximal portion of the clamp arm.

19. A surgical instrument comprising:
(a) an ultrasonic transducer;
(b) a shaft extending distally relative to the ultrasonic transducer; and
(c) an end effector arranged at a distal end of the shaft, wherein the end effector comprises:
   (i) an ultrasonic blade extending along a centerline and configured to be driven by the ultrasonic transducer with ultrasonic energy, wherein the ultrasonic blade comprises:
      (A) a linear proximal blade portion,
      (B) a curved distal blade portion,
      (C) a first lateral side, and
      (D) a second lateral side arranged opposite of the first lateral side, and
   (ii) a clamp arm movable relative to the ultrasonic blade for clamping tissue therebetween, wherein the clamp arm provides an RF electrode operable to seal tissue with RF energy, wherein the RF electrode comprises:
      (A) a first electrode side portion, wherein the first electrode side portion is spaced laterally outward from the first lateral side of the ultrasonic blade by a first lateral gap distance in a plane transverse to the centerline, and
      (B) a second electrode side portion spaced from the first electrode side portion, wherein the second electrode side portion is spaced laterally outward from the second lateral side of the ultrasonic blade by a second lateral gap distance in the plane transverse to the centerline,
   wherein each of the first and second lateral gap distances in the plane transverse to the centerline are equal along at least a portion of the curved distal blade portion, and
   wherein at least one of the first lateral gap distance or the second lateral gap distance is in the range of 0.002 inches to 0.012 inches along the curved distal blade portion.

20. The surgical instrument of claim 19, wherein a lateral width of at least one of the first electrode side portion or the second electrode side portion is in the range of 0.007 inches to 0.018 inches along the curved distal blade portion.

\* \* \* \* \*